United States Patent [19]

de Buda et al.

[11] 4,382,383

[45] May 10, 1983

[54] PIPE INSPECTION DEVICE

[76] Inventors: Eric G. de Buda, 55 Humberview Rd., Toronto, Ontario, Canada, M6S 1W7; Anthony L. Allen, 2335 Lakeshore Blvd., West, Apt. 406, Toronto, Ontario, Canada, M8V 1B9

[21] Appl. No.: 260,013

[22] Filed: May 4, 1981

[30] Foreign Application Priority Data

Feb. 25, 1981 [CA] Canada .................................. 371677

[51] Int. Cl.³ ............................................. G01N 29/04
[52] U.S. Cl. ....................................... 73/592; 73/623; 250/358.1
[58] Field of Search ................. 73/622, 623, 592, 638; 250/358 P; 138/90, 93

[56] References Cited

U.S. PATENT DOCUMENTS 3,483,466 12/1969 Crouch et al. .
3,584,504 6/1971 Proctor et al. .
3,766,775 10/1973 Gunkel .
4,006,359 2/1977 Sullins et al. ..................... 250/358 P
4,162,635 7/1979 Triplett et al. .

FOREIGN PATENT DOCUMENTS 54-109490 8/1979 Japan .................................... 73/623
54-139786 10/1979 Japan .................................... 73/623

Primary Examiner—Anthony V. Ciarlante
Attorney, Agent, or Firm—Ridout & Maybee

[57] ABSTRACT

An inspection device for use in scanning the interior of a pipe at a remote location is accurately centered within the pipe at the required location by two spiders. Each spider has three sickle-shaped arms which can be extended and retracted between operative and inoperative positions. The six spider arms are interconnected by a crank mechanism which ensures that all the arms move in unison between their limit positions.

7 Claims, 7 Drawing Figures

PIPE INSPECTION DEVICE

This invention relates to an inspection device for use in scanning the interior of pipelines. The sensing equipment of the device, that is, the item which actually emits and receives signals for monitoring the condition of the pipe, may be of any known type and is preferably an ultrasonic sensor of the type shown in U.S. Pat. No. 4,162,635, for example. The choice of sensor is not critical to the present invention.

One of the problems in using an ultrasonic sensor for monitoring the interior of a pipe at a remote location is to transport the sensor along the pipe to the required location. Another problem is to locate the sensor accurately on the axis of the pipe at the required location, since if it is located eccentrically false readings will be obtained. In a copending application filed concurrently herewith by E. G. de Buda, J. R. Boon and M. P. Dolbey entitled "Pneumatically Operated Pipe Crawler", there is described a device for dealing with the first of these problems. The present invention is concerned specifically with a centering arrangement for dealing with the second problem.

An inspection device in accordance with the present invention comprises a cylindrical housing defining a central axis, first and second end portions mounted at the ends of the housing coaxially therewith, a scanning probe journalled in the second end portion for rotation about the central axis, the probe extending from the second end portion, drive means mounted within the housing and being coupled to the probe for causing its rotation, and means for centering the device coaxially within a pipe being inspected. The centering means comprises a plurality of identical spider arms which are pivotally connected to the device for pivotal movement about respective pivotal axes which are spaced symmetrically about the central axis. A drive motor mounted within the housing is coupled to the spider arms by a coupling means constraining the arms to move pivotally in unison between radially extended and retracted positions.

Preferably there are two sets of spider arms which are pivotally connected to the first and second end portions of the device.

In a preferred embodiment of the invention the coupling comprises three axially extending shafts which are journalled in the first and second end portions for rotational movement about the respective pivotal axes of the spider arms, each shaft being common to a spider arm of the first set and a corresponding spider arm of the second set. Each shaft has an intermediate crank portion, the crank portions being of equal throw and being parallel to one another, the crank portions being rigidly interconnected to maintain their parallel relationship. The drive motor has an axially extending drive shaft with a crank portion of the same throw as the other crank portions and lying parallel thereto, all four crank portions being rigidly interconnected so that their parallel relationship is maintained.

In order that the invention may be readily understood, one embodiment thereof will now be described by way of example with reference to the accompanying drawings, in which.

Figure 1:
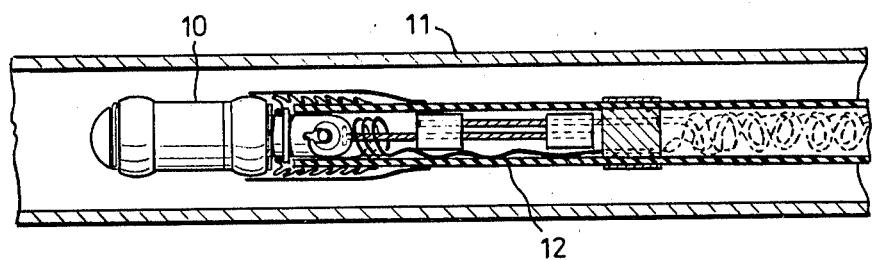
FIG. 1 shows an inspection device according to the invention supported at the leading end of a pipe crawler for feeding the device along the pipe.
Figure 2:
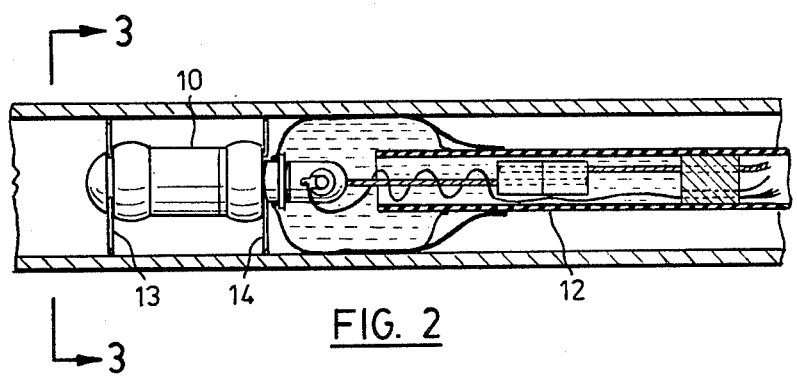
FIGS. 2 and 3 show the device located centrally at a required position.
Figure 6:
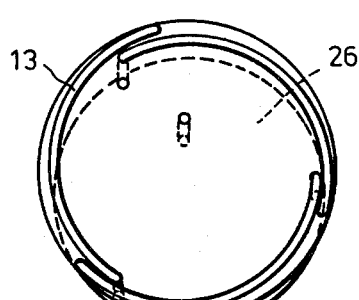
FIG. 6 is a view on line 6—6 in FIG. 5.
Figure 7:
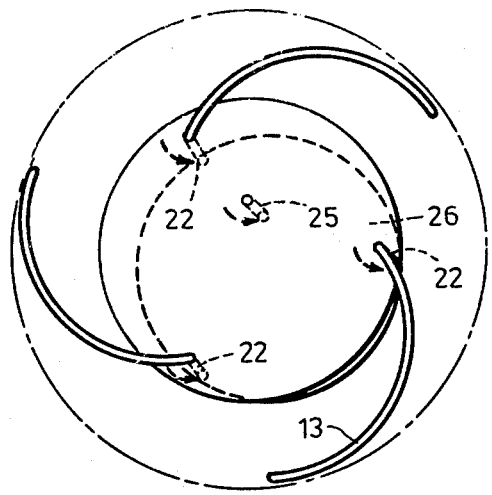
FIG. 7 is a view corresponding to FIG. 6 but with the spider arms extended.
Figure 3:
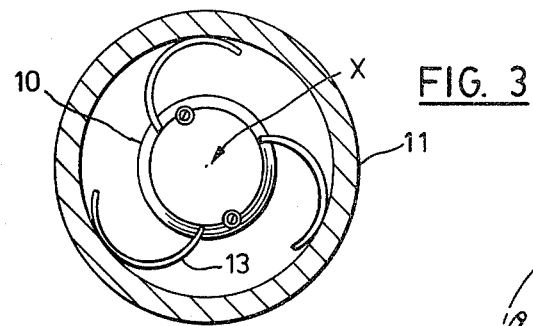

Referring to the drawings, FIG. 1 shows the inspection device 10 being moved along the interior of a pipe 11 by means of a pipe crawler 12. While the device is being so moved along the pipe, the spider arms are retracted. FIG. 2 shows the device 10 located at a required position, the device being accurately centered within the pipe by a first set of spider arms 13 and a second set of spider arms 14. As shown in FIG. 3, there are three spider arms in each set. These arms are sickle-shaped and are pivotally connected at their ends to the body of the device 10 for pivotal movement about respective pivotal axes which are symmetrically spaced around the central axis X of the device.

Figure 4:
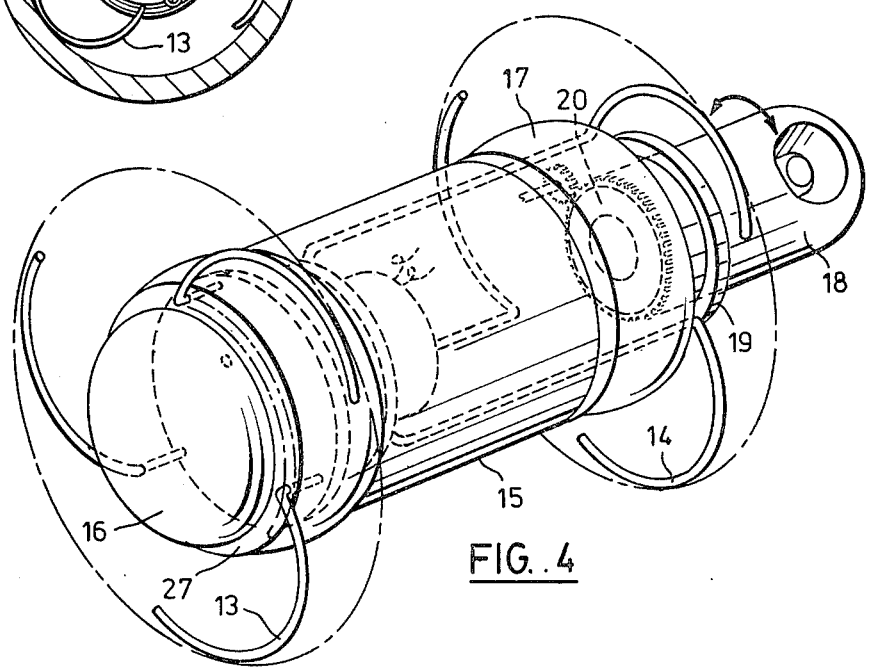
FIGS. 4 and 5 are elevational views of the inspection device.

Referring to FIG. 4, the device has a cylindrical housing portion 15 which defines the central axis X of the device, a bullet-shaped leading end portion 16 mounted at the leading end of the housing 15, and an end portion 17 mounted at the trailing end of the housing. The end portions 16 and 17 are arranged coaxially with the housing 15 and with one another. A rotary probe 18, which houses the ultrasonic sensor, extends axially from the trailing end of the device and is journalled for rotation in a projecting collar 19 of the end portion 17. The probe 18 is driven by an electric motor (not shown) mounted in the housing 15, through transmission gearing 20.

Figure 5:
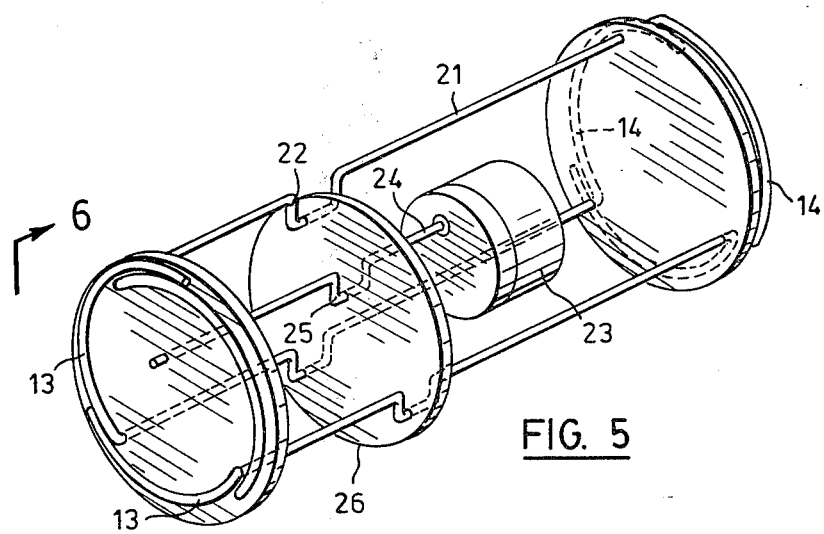

The three sickle-shaped spider arms 13 are pivotally connected to the leading end portion 16, while the identical set of spider arms 14 are pivotally connected to the rear end portion 17. As best shown in FIG. 5, each spider arm 13 is connected directly to a corresponding spider arm 14 of the other set, for common rotary movement therewith, by means of an axially extending shaft 21, this shaft being journalled at its ends in the end portions 16, 17. Each of the shafts 21 has an intermediate crank portion 22, the crank portions of the three shafts having the same throw and being oriented parallel to one another. A drive motor 23 mounted within the housing 15 has a drive shaft 24 which extends axially, this shaft 24 also having a crank portion 25 which is identical to the crank portions 22 and similarly oriented. The four crank portions 22, 25 are rigidly interconnected, i.e. their positions relative to one another are maintained constant, by a rigid rotary member such as a disc 26 having four holes through which the crank portions extend and in which they are journalled. Thus, when the motor 23 rotates the shaft 24, the disc 26 is caused to orbit without rotating in a plane perpendicular to the central axis of the device, the radius of the orbit being determined by the throw of the crank portion 25. As the disc 26 interconnects the crank portions 22, these in turn are caused to rotate, causing the spider arms 13 and 14 to be moved outwards and inwards in unison between their radially extended and retracted positions.

The leading end portion 16 provides an annular recess 27 in which the spider arms 13 are accommodated when retracted to the position shown in FIG. 5. The trailing end portion 17 has a stepped diameter where it meets the collar 19; this step provides in effect a recess which accommodates the spider arms 14 when they are retracted, the arms thus being sheltered behind the larger diameter portion of the member 17.

What we claim is:

1. An inspection device for use in scanning the interior of a pipe, comprising:
   a cylindrical housing defining a central axis,
   a first end portion mounted at one end of the housing coaxially therewith,
   a second end portion mounted at the other end of the housing coaxially therewith,
   a scanning probe journalled in said second end portion for rotation about said central axis, the probe extending axially from the second end portion,
   drive means mounted within the housing, said drive means being coupled to the probe for effecting rotation thereof, and
   means for centering the device coaxially within a pipe, said means comprising:
   a plurality of identical spider arms pivotally connected to the device for pivotal movement about respective pivotal axes parallel to and spaced symmetrically about said central axis,
   a drive motor mounted within the housing, and
   coupling means connected between the motor and the spider arms for effecting pivotal movement of the arms, said motor being capable of selectively extending and retracting said spider arms between radially extended and retracted positions and said coupling means constraining the spider arms to move pivotally in unison between said radially extended and retracted positions.

2. An inspection device according to claim 1, wherein the plurality of spider arms comprises a first set of spider arms pivotally connected to said first end portion of the device, and a second set of spider arms pivotally connected to said second end portion of the device, the pivotal axes of the first set of arms being aligned with the pivotal axes of the second set of arms.

3. An inspection device according to claim 2, wherein each set comprises three spider arms.

4. An inspection device according to claim 3, wherein each end portion provides a recess for accommodating the spider arms in their retracted position, the spider arms being sickle-shaped so as to lie in the recesses when retracted.

5. An inspection device according to claim 4, wherein said coupling means comprises three axially extending shafts journalled in said end portions for rotational movement about said respective pivotal axes, each shaft being connected to a spider arm of the first set and a corresponding spider arm of the second set, each shaft having an intermediate crank portion, the crank portions being of equal throw and being parallel to one another, and means rigidly interconnecting the crank portions to maintain their parallel relationship.

6. An inspection device according to claim 5, wherein the drive motor is connected to the coupling means by an axially extending drive shaft having a crank portion of the same throw as the other crank portions and being parallel thereto, said interconnecting means rigidly interconnecting all four crank portions to maintain their parallel relationship.

7. An inspection device according to claim 6, wherein said first end portions is bullet-shaped, constituting the leading end of the device.

* * * * *